(12) United States Patent
Whittaker et al.

(10) Patent No.: US 7,491,206 B2
(45) Date of Patent: *Feb. 17, 2009

(54) ADJUSTABLE DRILL GUIDE ASSEMBLY AND METHOD OF USE

(75) Inventors: Gregory R. Whittaker, Stoneham, MA (US); Thomas C. May, Wrentham, MA (US)

(73) Assignee: Ethicon, Inc., Somerville, NJ (US)

( * ) Notice: Subject to any disclaimer, the term of this patent is extended or adjusted under 35 U.S.C. 154(b) by 349 days.

This patent is subject to a terminal disclaimer.

(21) Appl. No.: 10/609,013

(22) Filed: Jun. 27, 2003

(65) Prior Publication Data

US 2004/0267273 A1 Dec. 30, 2004

(51) Int. Cl.
*A61B 17/58* (2006.01)
(52) U.S. Cl. ............................................. 606/98
(58) Field of Classification Search .................. 606/79, 606/80, 86–89, 96–98; 623/13.14; 128/898
See application file for complete search history.

(56) References Cited

U.S. PATENT DOCUMENTS

| | | | | |
|---|---|---|---|---|
| 4,667,664 A | * | 5/1987 | Taylor et al. | 606/64 |
| 5,312,409 A | * | 5/1994 | McLaughlin et al. | 606/86 |
| 5,350,380 A | * | 9/1994 | Goble et al. | 606/80 |
| 5,354,300 A | * | 10/1994 | Goble et al. | 606/80 |
| 5,649,930 A | * | 7/1997 | Kertzner | 606/96 |
| 5,688,284 A | | 11/1997 | Chervitz et al. | |
| 5,849,013 A | | 12/1998 | Whittaker et al. | |
| 5,891,150 A | | 4/1999 | Chan | |
| 6,066,173 A | | 5/2000 | McKernan et al. | |
| 6,113,604 A | | 9/2000 | Whittaker et al. | |
| 6,325,804 B1 | * | 12/2001 | Wenstrom et al. | 606/72 |
| 6,379,384 B1 | | 4/2002 | McKernan et al. | |
| 6,514,253 B1 | | 2/2003 | Yao | |
| 6,517,546 B2 | | 2/2003 | Whittaker et al. | |
| 6,540,783 B1 | | 4/2003 | Whittaker et al. | |
| 2002/0173849 A1 | * | 11/2002 | McKernan et al. | 623/13.14 |
| 2003/0065391 A1 | * | 4/2003 | Re et al. | 623/13.14 |

* cited by examiner

*Primary Examiner*—Eduardo C Robert
*Assistant Examiner*—Michael J Araj
(74) *Attorney, Agent, or Firm*—Nutter McClennen & Fish LLP

(57) ABSTRACT

An adjustable drill guide is provided that can be used to deliver a cross pin at a distance near the entrance to the femoral bone tunnel during ligament surgery. The cross pin positioned at the joint line, or tunnel opening, compresses and secures the graft within the bone tunnel, thereby preventing the graft from swaying back and forth post surgery when the joint is in motion. The adjustable drill guide assembly comprises a guide frame that includes an arm portion and a base portion that extends transversely to the arm portion. A rod member connects to the base portion for extending into the bone tunnel of the bone. Also included is a guide member configured for connection to the arm portion. The guide member is configured to be in moveable and lockable disposition along a length of the arm portion.

16 Claims, 6 Drawing Sheets

ADJUSTABLE DRILL GUIDE ASSEMBLY AND METHOD OF USE

CROSS-REFERENCE TO RELATED APPLICATIONS

Not applicable.

STATEMENT REGARDING FEDERALLY SPONSORED RESEARCH

Not Applicable.

FIELD OF THE INVENTION

The present invention relates to surgical methods and apparatus in general, and more particularly to methods and devices for fixing tissue grafts in bone tunnels. Even more particularly, this invention relates to an adjustable drill guide for use in the placement of cross pins to secure a tissue graft within a bone tunnel near the tunnel entrance.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

In the case of a partial detachment, the injury frequently heals itself if given sufficient time, and if care is taken not to expose the injury to undue stress during the healing process. If, however, the ligament or tendon is completely detached from its associated bone or bones, or if it is severed as the result of a traumatic injury, partial or permanent disability may result. Fortunately, a number of surgical procedures exist for reattaching such detached tissues and/or completely replacing severely damaged tissues. Typically, these procedures can involve the re-attachment of the detached tissue using attachment devices such as staples, sutures and/or cancellous bone screws. Such attachment devices have also been used to attach tendon or ligament grafts (often formed from autogeneic tissue harvested from elsewhere in the body) to the desired bone or bones.

A common injury where treatment requires the reattachment of soft tissue to bone is anterior cruciate ligament (ACL) damage in a human knee. Several methods for repairing an ACL injury are known in the art, and typically involve the replacement of the damaged or torn ligament with a tissue graft by first forming bone tunnels through the tibia and/or femur at the points of normal attachment of the anterior cruciate ligament. Next, a ligament graft is harvested and prepared for insertion into the bone tunnel. The graft can be folded over and secured at its folded end to a graft anchor device using suture thread. For instance, a graft attachment device can be used to anchor the folded end of the graft to the femur. In a typical graft attachment device, the folded end is held to the graft anchor device by a suture thread, while the graft attachment device is anchored to the femur outside the bone tunnel exit. Then, a screw or cross pin is inserted through the bone tunnel and graft so as to intersect through the bone tunnel and secure the graft in position within the tunnel by a tight interference fit. The pin compresses and suspends the graft at this graft-tunnel interface. Finally, the free end of the graft ligament is securely attached to the tibia.

An alternative method for securing a graft inside a bone tunnel of a femur involves inserting a folded graft, folded end first, into a bone tunnel, and then securing the folded end by placing a cross pin through the graft and between the folds. Often, the graft is also stitched together, folded over, and the ends whip stitched to form a graft bundle. Since the graft is essentially folded over the cross pin inside the bone tunnel, the graft acts as a "slingshot" and can therefore stretch and bend during flexion of the knee joint. An additional cross pin can optionally be inserted to additionally secure the graft to the femur.

In order to provide for proper cross-pinning of the graft in the bone tunnel, a drill guide is generally used. The drill guide serves to ensure that the pin transversely passes the bone so that it will intersect the appropriate tunnel section and the graft. Drill guides for use in effecting such transverse drilling, as well as methods for using such guides in an ACL repair surgery, are described, for example, in U.S. Pat. Nos. 6,540,783, 6,517,546, 6,379,384, 6,113,604, 6,066,173, and 5,849,013, all of which are hereby incorporated by reference.

A potential problem with the current techniques for femoral fixation of a soft tissue graft during ligament (e.g., ACL) reconstruction surgery is that the point of fixation, i.e., where the graft is secured, is relatively far from the joint line. That is, the graft is secured relatively near the bone tunnel exit. Because the graft is not-compressed and suspended near the bone tunnel entrance, the graft does not reside in a tight interference fit at this portion of the bone tunnel. During flexion and movement of the knee joint, this unsecured portion of the graft tends to sway back and, forth, causing a "windshield wiper" effect that can ultimately result in the erosion and weakening of the graft near the joint line. Often referred to as the "bungie cord" effect, this swaying motion can also lead to tunnel widening. Furthermore, if the graft does not form a tight fit with: the bone tunnel at the entrance, synovial fluid can enter, the tunnel and impregnate the graft and thus render the graft ineffective.

SUMMARY OF THE INVENTION

The present invention provides an adjustable drill guide that can be used to deliver a cross pin at a distance near the entrance to the femoral bone tunnel during ligament (e.g., ACL) reconstruction surgery. The cross pin positioned at the joint line, or-tunnel opening, compresses and secures the graft within the bone tunnel, thereby preventing the graft from swaying back and forth when the joint is in motion. In an exemplary embodiment of the present invention, an adjustable drill guide assembly is provided for forming a transverse bore through a bone tunnel of a bone. The adjustable drill guide assembly comprises a guide frame that includes an arm portion and a base portion that extends transversely to the arm portion. Also included is a rod member that is connectable to the base portion. The rod member extends transversely to the base portion and parallel to the arm portion when connected to the base portion. The rod member is defined by an elongated stem portion for extending into the bone tunnel of the bone. The adjustable drill guide assembly also includes a guide member configured for connection to the arm portion. The guide member includes a channel extending therethrough at an angle normal to a longitudinal axis of the arm portion when the guide member is connected to the arm portion. The guide member is configured to be in moveable and lockable disposition along a length of the arm portion.

In an aspect of the embodiment, the arm portion includes indicia representing the relative height of the channel with respect to the bone tunnel when the elongated stem portion is inserted inside the bone tunnel. In another aspect, the channel is configured to receive a trocar sleeve assembly. The trocar sleeve assembly comprises a trocar having a pointed distal end, a proximal end, an elongated body extending therebetween, and a sleeve disposed over the elongated body of the trocar. The channel is configured to allow moveable displacement, i.e., slidability, of the trocar sleeve assembly through the guide member. In yet another aspect, the rod member further includes, an enlarged head portion at a free end. The enlarged head portion has an aperture that is sized and configured for passage of the trocar sleeve assembly there through. In one embodiment of the present invention, the guide member includes two channels, and the assembly includes two trocar sleeve assemblies for placement of a trocar sleeve assembly in each channel. The aperture of the enlarged head portion is thus sized to allow passage of two trocar sleeve assemblies therethrough.

In another aspect of the present invention, the rod member is a cannulated rod to allow for the passage of a guidewire therethrough. In still another aspect, the trocar is removable from the sleeve so as to allow just the sleeve to remain within the guide member. In still yet another aspect of the invention, the guide member is configured to be slidably disposed along the length of the arm portion. The guide member can further include a locking mechanism (e.g., a set screw) for locking the guide member along the length of the arm portion.

Also provided is a method for fixing a tissue graft within a bone tunnel in a femoral bone. The method comprises the steps of preparing a bone tunnel in the bone for insertion of a tissue graft, and providing pan adjustable drill guide assembly including a guide frame having an arm portion and a base portion that extends transversely to the arm portion, a rod member for connection to the base portion, the rod member extending transversely to the base portion and parallel to the arm, portion when connected to the base portion, and further having an elongated stem portion for extending into the bone tunnel of the bone, and a guide member configured for connection to the arm portion, the guide member including a channel extending therethrough at an angle normal to a longitudinal axis of the arm portion when the guide member is connected to the arm portion, wherein the guide member is configured to be in moveable and lockable disposition along a length of the arm portion. Using the drill guide assembly, a bore transverse to the bone tunnel is, drilled. The tissue graft is then placed inside the bone tunnel, and secured within the bone tunnel at the location of the bore.

In an aspect of the present invention, the bore is drilled by placing the elongated stem portion into the bone tunnel, locking the guide member onto the arm portion, inserting a drill bit through the channel of the guide member, and drilling the bore so that the drill bit extends transversely through the bone tunnel. In another aspect, the method further includes the step of adjusting the guide member along the length of the arm portion, locking the guide member at another position on the arm portion, and drilling another bore transverse to the bone tunnel. The bore can extend transversely through the bone tunnel at a location near the bone tunnel entrance. In addition, the bore can extend transversely through the bone tunnel at a location near the bone tunnel exit.

In yet another aspect of the present invention, the tissue graft is secured by placing a cross pin through the bore to compress the tissue graft within the bone tunnel. In still yet another aspect, the tissue graft can further be secured to the femoral bone at a point near the bone tunnel exit. For instance, the tissue graft can be further secured using an external fixation device attached to the tissue graft. The external fixation device can anchor the tissue graft to a portion of the bone outside of the bone tunnel.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying exemplary drawings, though not necessarily drawn to scale, in which:

FIG. 3F shows a graft completely attached within the bone tunnel of the femoral bone of FIG. 3C; and.

DETAILED DESCRIPTION OF THE INVENTION

Figures 1A, 1B:
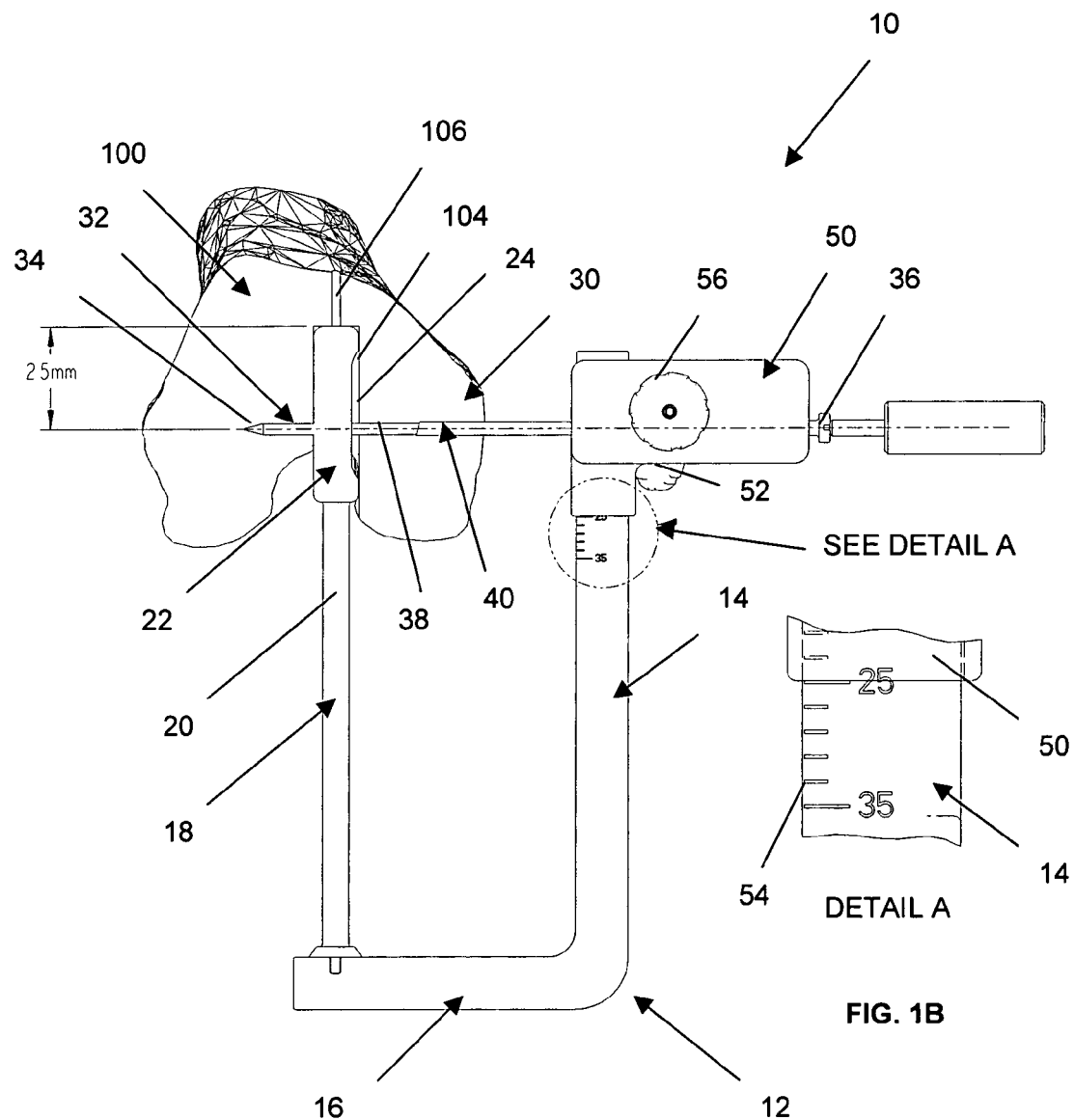
FIG. 1A is perspective view of the adjustable drill guide assembly of the present invention.
FIG. 1B is an enlarged view of a portion of the adjustable drill guide assembly of FIG. 1A.

In FIG. 1A, an adjustable drill guide assembly 10 of the present invention is shown. As illustrated, the drill guide assembly 10 can be used for drilling bores through a bone (e.g., femoral bone 100) of a patient. As are commonly used in the art, a prepared bone tunnel 102 is shown within the bone 100 to receive a tissue graft. The bone tunnel 102 comprises a first portion 104 that includes the opening of the tunnel, and a second portion 106 that leads to the tunnel exit, i.e., the outside of the bone 100. The first portion 104 is wider than the second portion 106 and is configured to receive the graft, while the second portion 106 is narrower and typically is configured to receive either a guide wire (in the case of a slingshot-type procedure), or a suture strand attached to the graft (in the case where the procedure also utilizes a graft attachment device). The suture strand can be secured by means of graft attachment devices that anchor the suture strand to the bone 100.

Turning now in particular to the adjustable drill guide assembly 10 of the present invention, the assembly 10 comprises a guide frame 12 that includes an arm portion 14 and a base portion 16 that extends transversely to the arm portion 14. A rod member 18 connects to the base portion 16. The rod member 18 extends transversely to the base portion 16 and parallel to the arm portion 14 when connected to the base portion 16. The rod member 18 is defined by an elongated stem portion 20 for extending into the prepared bone tunnel 102 of the bone 100. The elongated stem portion 20 extends to an enlarged head portion 22 at a free end of the rod member 18. The enlarged head portion 22 is sized and configured to abut the top of the bone tunnel 102 in the first portion 104. Assembly 10 can be provided with a plurality of rod members 18, each of which can have a different length for use in different sized patients. The rod members 18 are configured so as to be detachable from the base portion 16, using an attachment mechanism that can comprise any suitable means as is well known in the art. The enlarged head portion 22 of the rod members 18 also includes an aperture 24 that is sized and configured for passage of a trocar 32 of a trocar sleeve assembly 30 transversely therethrough. Preferably, the rod member 18 is also a cannulated rod to allow for the insertion of a guidewire therethrough.

The trocar sleeve assembly 30 comprises a trocar 32 having a pointed distal end 34, a proximal end 36, an elongated body 38 extending therebetween, and a sleeve 40 disposed over the elongated body 38 of the trocar 32. The trocar 32 is configured to be removable from the sleeve 40. The trocar sleeve assembly 30 is held on the guide frame 12, by guide member 50. As illustrated in FIG. 1A, the guide member 50 is configured for connection to the arm portion 14 of the guide frame 12. Within the guide member 50 are channels that extend through at an angle normal to the longitudinal axis of the arm portion 14 when the guide member is connected to the arm portion 14. The channels are configured to allow moveable displacement, i.e., slidability, of the trocar sleeve assembly 30 through the guide member 50. Preferably, two channels are provided within the guide member 50, although it is contemplated that one or more channels can be provided. The aperture 24 of the enlarged head portion 22 should be complementarily sized so as to accommodate the passage of the trocar sleeve assemblies 30 therethrough. A locking mechanism 56 such as a set screw can be provided to secure the trocar sleeve assembly 30 within the channel of the guide member 50.

As illustrated, the guide member 50 is configured to be in moveable and lockable disposition along the length of the arm portion 14. It is contemplated that the guide member 50 can be slidable over the arm portion 14 and can be locked at a specific location using a locking mechanism such as a set screw 52 as is commonly used in the art. This adjustability enables the surgeon to move the guide member 50 up or down the arm portion 14 and to lock in place the guide member at a desired location for placing a cross pin. As shown in detail in FIG. 1B, the arm portion 14 includes indicia 54 representing the relative height of the channel with respect to the bone tunnel 102 when the elongated stem portion 20 is inserted inside, the bone tunnel 102. In the illustrated example, where a cross pin is to be placed at a location; 25 mm from the top of the first portion 104 of the bone tunnel 102, the surgeon locks the guide member 50 at the mark indicating 25 mm and drills through the channel at this position. It is contemplated that cross pins will be placed approximately 3-5 mm from the bone tunnel entrance in a bone tunnel having a depth in the range of about 25-30 mm.

The adjustable drill guide assembly 10 of the present invention can be used, for example, in femoral fixation of a graft during ACL reconstruction surgery. As previously mentioned, the adjustable drill guide assembly 10 provides an advantage over the drill guide assemblies currently available because the guide member 50 is able to adjust up or down the length of the guide frame 12, thereby allowing a surgeon to place a cross pin near the bone tunnel entrance in a femoral fixation procedure. The method for performing this procedure can-best be described by referring to FIGS. 3A-3G which show the basic steps in a slingshot-type procedure, for securing a graft inside a bone tunnel of a femur.

Figures 2A, 2B, 2C:
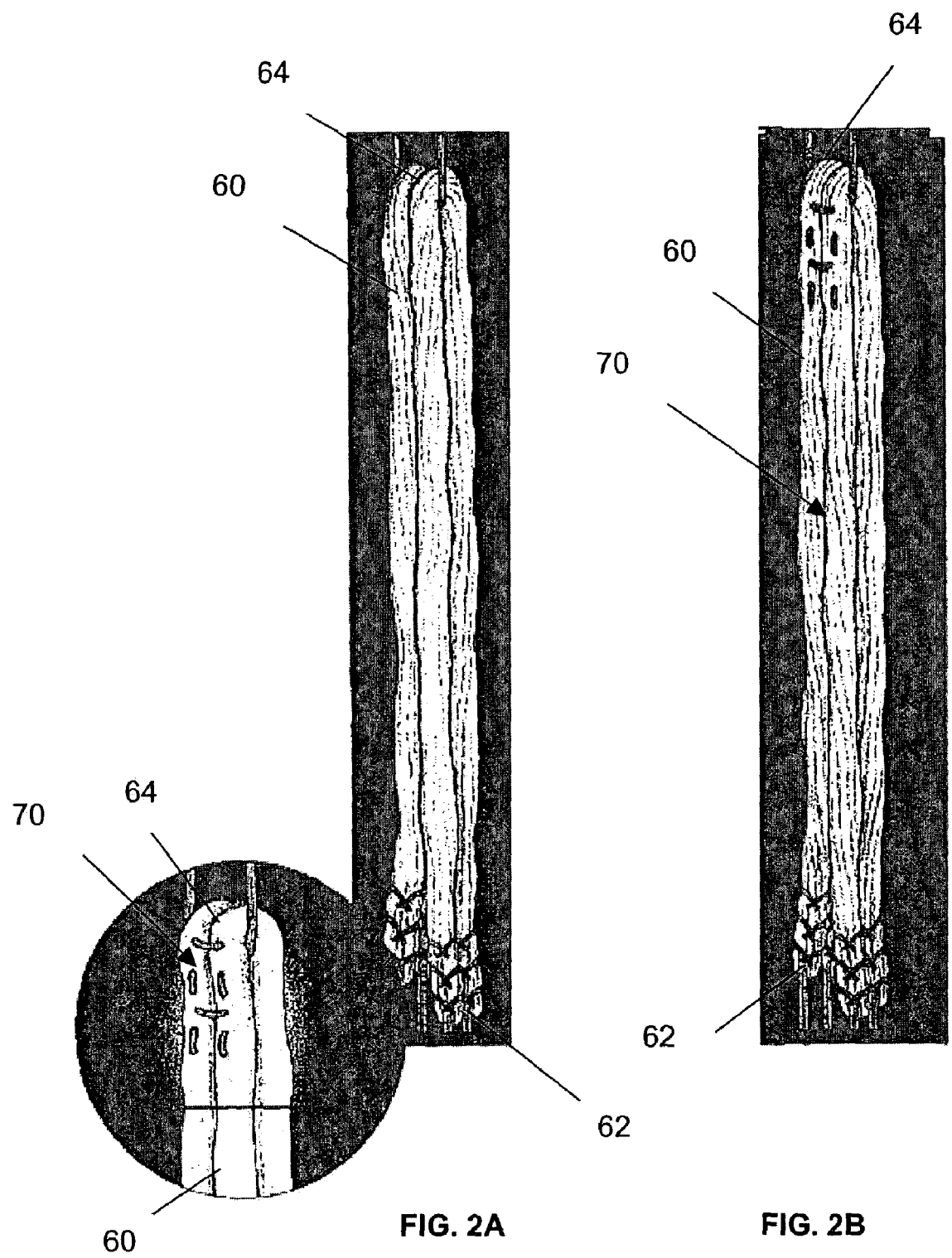
FIG. 2A shows a graft with whip stitching.
FIG. 2B shows the graft of FIG. 2A with further whip stitching.
FIG. 2C shows an enlarged view of the folded end of graft of FIG. 2B.

Turning now to FIG. 2A, tissue 60 is first harvested from the patient or a suitable donor Source. Specifically, tendon can be harvested from the semitendinosus (semi-t) and gracilis tendons of the patient. Once retrieved, the tendons 60 are prepared to form the final graft 70 to be placed inside the bone tunnel 202. The ends 62 of the harvested tendons 60 are whip stitched using suture thread. The tendons 60 are then folded over a suture thread as shown in FIG. 2A. Next, the folded-over portion of the tendons, i.e., the looped portion 64, is then whip stitched together to form a bundle as illustrated in FIG. 2B and in greater detail in FIG. 2C. Specifically, the semi-t is whip stitched to the semi-t, then the gracilis is whip stitched to the gracilis. Finally, the semi-t is whip stitched to the gracilis across the front and back to secure the two together. This whip stitched portion forms the part of the graft 70 that will be inserted into the femoral bone tunnel. By whip stitching the tendons together, the stitches ensure fixation within the bone tunnel when combined with the cross pin.

Figure 3A:
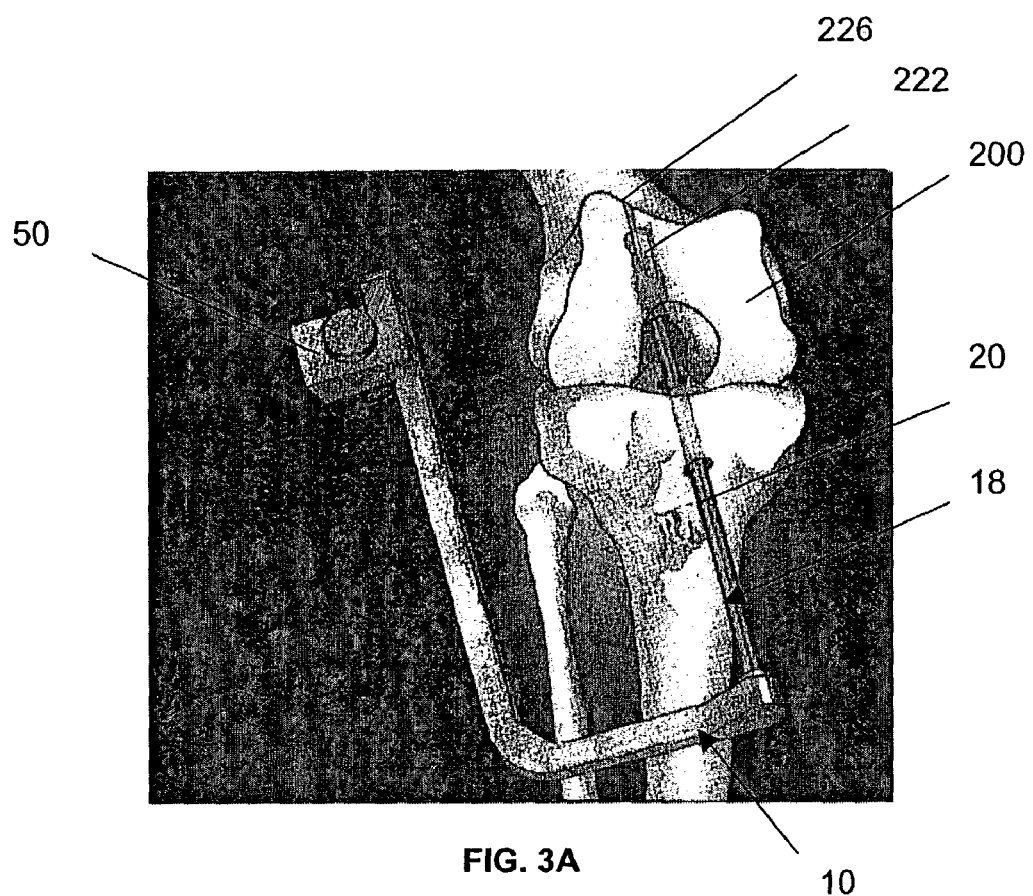
FIG. 3A shows a step of placing a drill guide assembly of the present invention inside a femoral bone tunnel.

During preparation of the graft 70, a femoral tunnel 202 is drilled up through the notch of the femoral bone 200. Typically, the tunnel 202 is drilled to a depth of about 30 mm, although other depths can be chosen as well. After the tunnel 202 is cleared of debris, an appropriate sized rod member 18 is attached to the drill guide assembly 10. A guidewire 226 placed through the bone tunnel 202 helps the rod member 18, which is cannulated and can be placed over the guidewire 226, to ease into the bone tunnel 202, as shown in FIG. 3A. The rod member 18 is advanced until the enlarged head portion 22 abuts the top of the first, wider portion of the bone tunnel 202. At this point, the guidewire 226 can be removed, leaving the rod member 18 inside the tunnel 202.

Figure 3B:
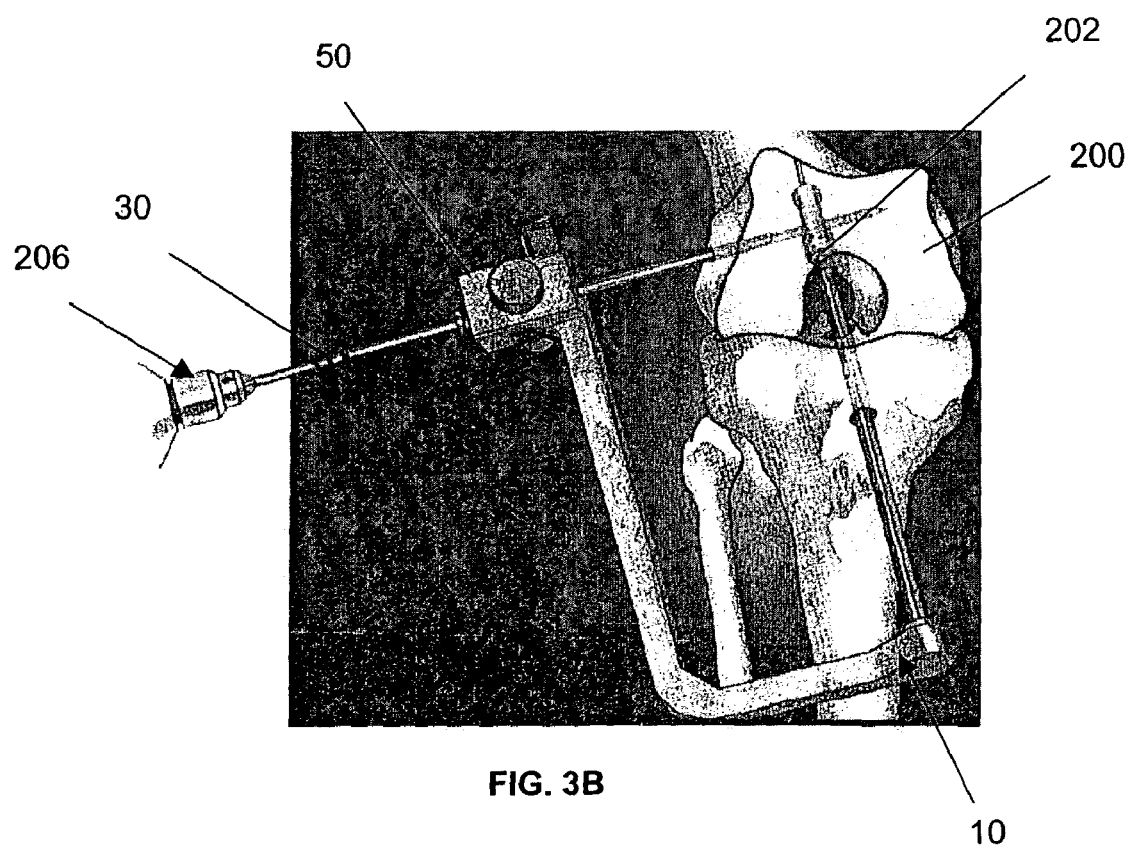
FIG. 3B shows a step of drilling a bore-into a femoral bone using the drill guide assembly of FIG. 3A.
Figure 3C:
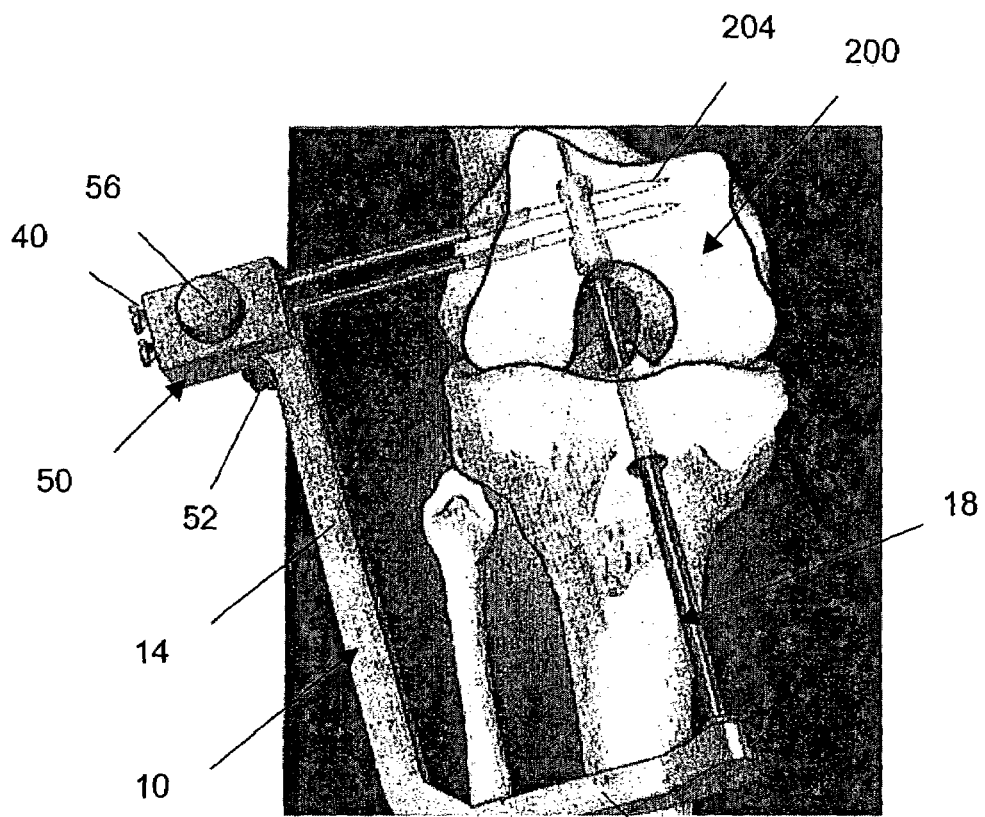
FIG. 3C shows a further step of preparing the bores of the femoral bone of FIG. 3A.

A trocar sleeve assembly 30 as shown in FIG. 3B can then be inserted through a channel within the guide member 50. The trocar sleeve assembly 30 can be connected to a drill 206 for drilling a bore 204 extending transverse to the bone tunnel 202. After the bore 204 has been drilled, the procedure can be repeated if a second bore 204 is desired. When all the necessary bores 204 have been drilled, the drill 206 is removed from the trocar sleeve assembly 30, along with the trocar 32, leaving only the sleeves 40 as illustrated in FIG. 3C. As shown, the sleeves 40 remain outside of the bone tunnel 202.

Figure 3D:
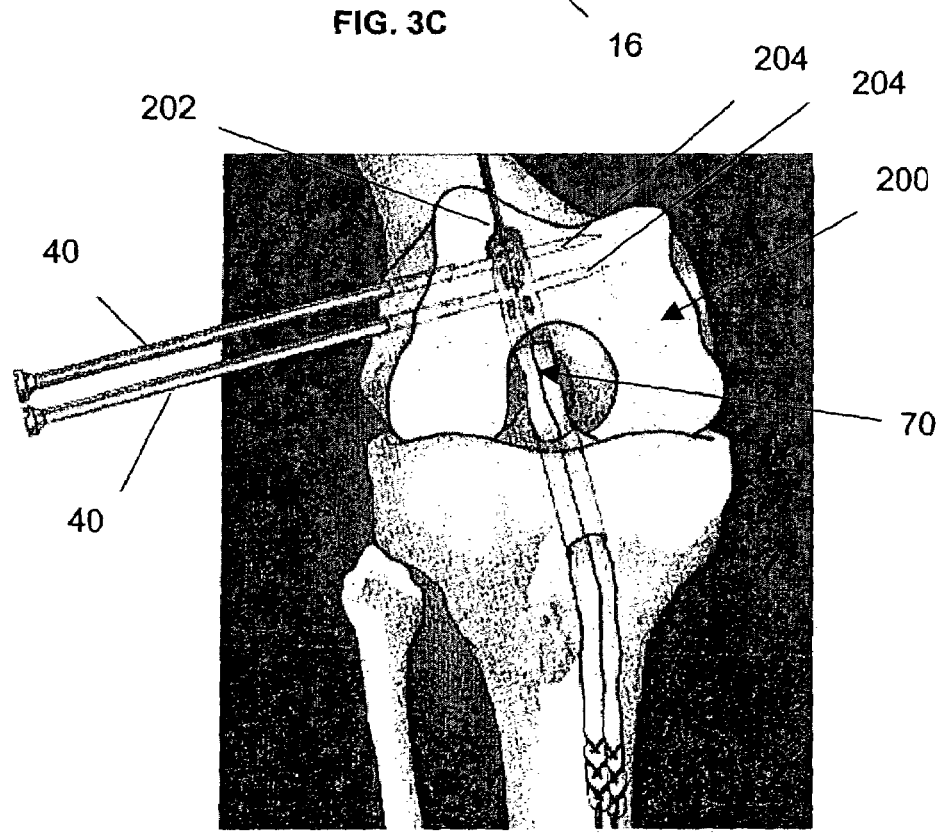
FIG. 3D shows a step of inserting a graft in a bone tunnel of FIG. 3C.
Figure 3E:
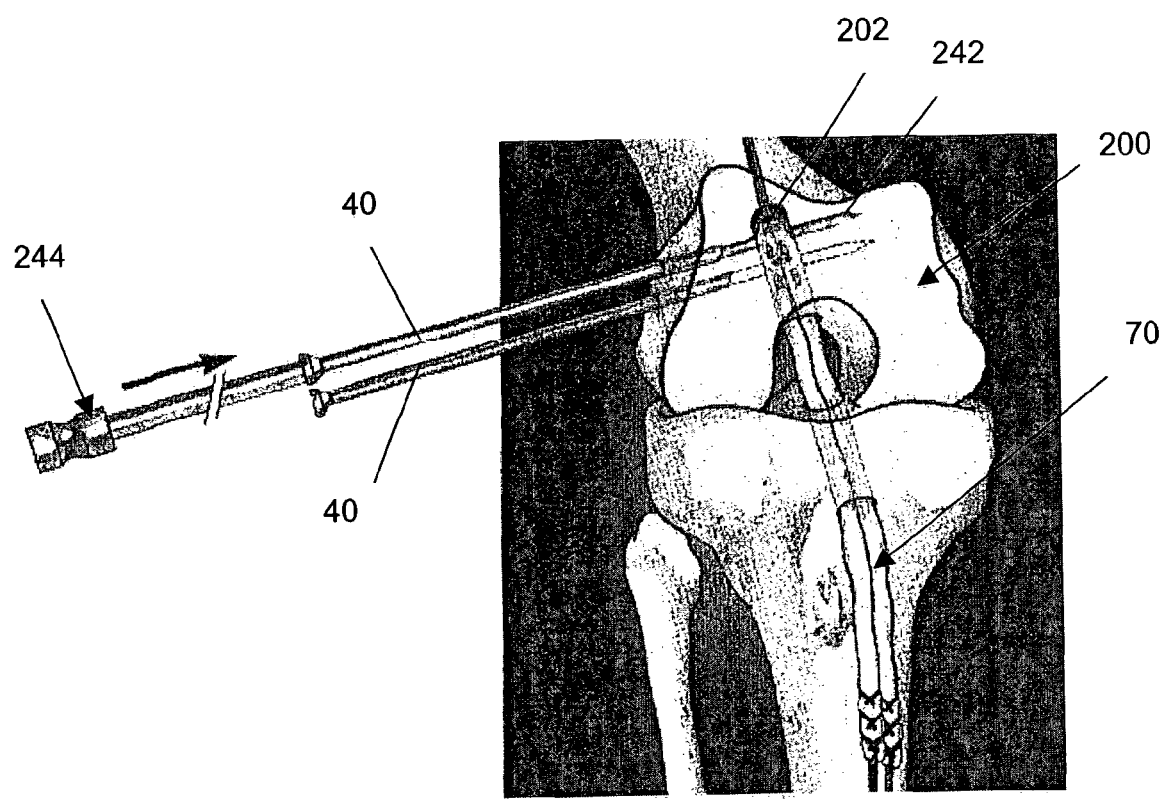
FIG. 3E shows a step of inserting a cross pin into the prepared bore of FIG. 3C.
Figure 3F:
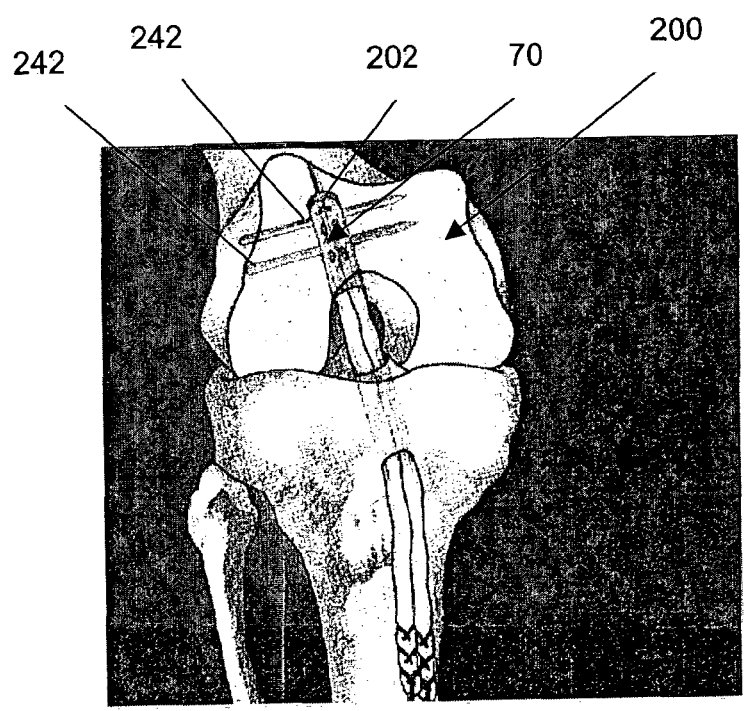

Next, the guidewire 226 is placed back into the bone tunnel 202 through the exit hole of the bone tunnel 202. The guidewire 226 should extend all the way down the cannulated rod member 218. The guide frame 12 and attached rod member 18 are then removed, leaving only the sleeves 40 and the guidewire 226. At this point, the prepared graft 70 can now be pulled into the tunnel 202 as shown in FIG. 3D. When the graft 70 is properly seated within the bone tunnel 202, cross pins 242 can be placed through the sleeves 40 using an inserter tool 244 as is well known in the art, and as shown in FIG. 3E. The cross pins 242 should extend all the way through the drilled bore 204, passing through the graft 70, and preferably in between the folds of the graft 70. The cross pins 242 compress the graft within the bone tunnel 202, as illustrated in FIG. 3F. When both cross pins 242 have been inserted, the sleeves 40 can be removed, leaving a fixed graft 70 in the femoral bone tunnel 202.

Figure 4:
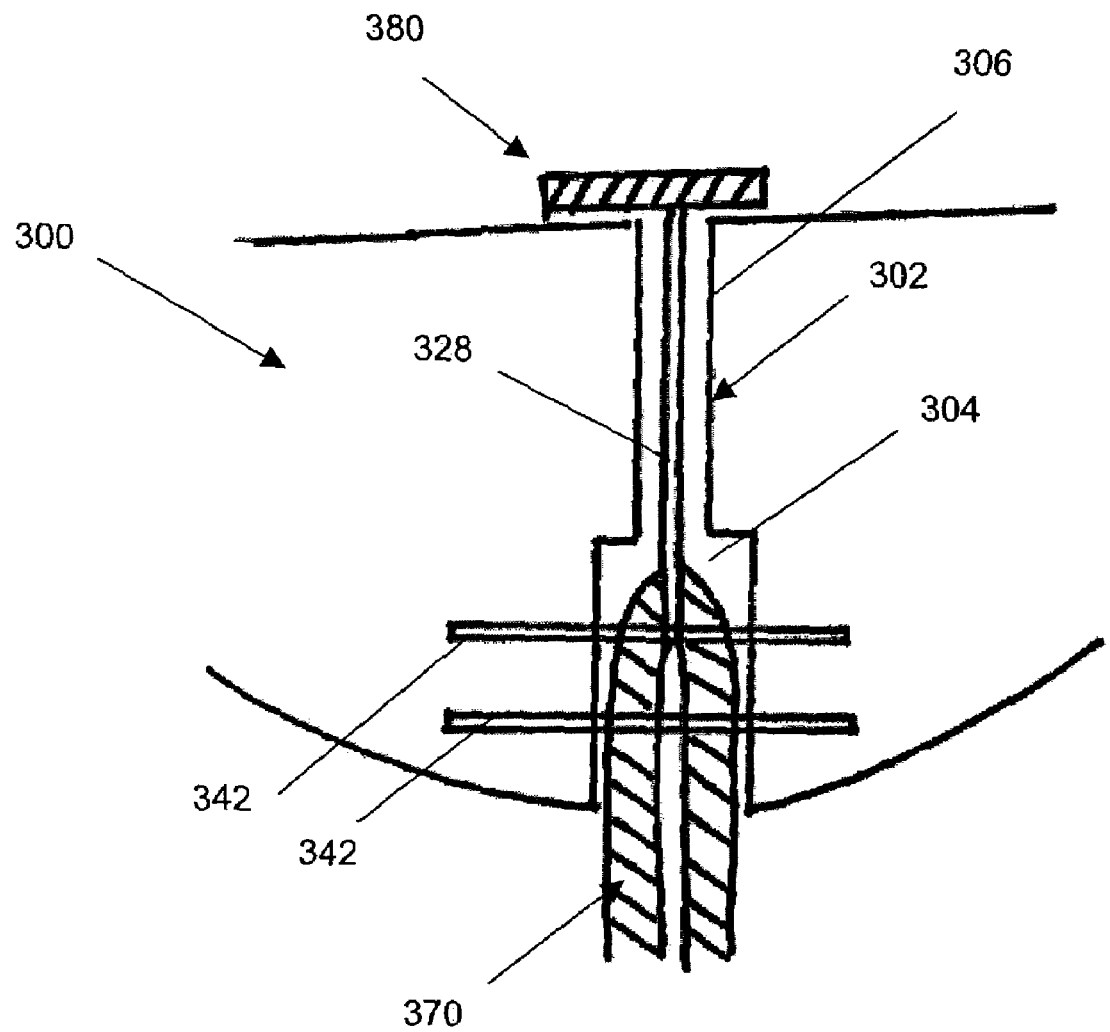
FIG. 4 shows another embodiment of a graft completely attached within a bone tunnel of a femoral bone in accordance with the method of the present invention.

The above steps can be applied to graft 370 that is additionally attached to a graft fixation device 380 using the adjustable drill guide assembly 10 of the present-invention. FIG. 4 shows a graft 370 secured inside a bone tunnel 362 of a femur 300 with cross pins 342 that were inserted using the adjustable drill guide assembly 10 of the present invention. By allowing bores to be drilled nearer the joint line, i.e., the bone tunnel entrance, cross pins 342 were able to be placed near the bone tunnel entrance. For a bone tunnel having a depth in the range of about 25 to 30 mm, it is contemplated that the cross pins can be placed about 3 to 5 mm away from the bone tunnel entrance.

As illustrated, graft 370 is compressed and suspended near the bone tunnel entrance, within the first portion 304 of the tunnel 302. This prevents the graft 370 from swaying back and forth, and eroding and weakening the graft 370 near the joint line. Securing the graft 370 at this position also prevents synovial fluid from entering the tunnel 302 and impregnating the graft 380. In the present embodiment, the graft 370 is further secured within the bone tunnel 302 with a graft attachment device 380 as shown. As is well known in the art, the graft attachment device 380 attaches to a suture thread-328 connected to the graft 370. The suture thread 328 extends up through the second, narrow portion 306 of the bone tunnel 302 and to the graft attachment device 380 Which is secured to the femur 300 outside of the bone tunnel 302.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An adjustable drill guide assembly for forming a transverse bore through a bone tunnel of a bone, comprising:
    a guide frame including an arm portion and a base portion that extends transversely to the arm portion;
    a rod member for connection to the base portion, the rod member extending transversely to the base portion and parallel to the arm portion when connected to the base portion, and further having an elongated stem portion for extending into the bone tunnel of the bone and having an enlarged head portion with an aperture extending therethrough for passage of a trocar sleeve assembly; and
    a guide member configured for connection to the arm portion, the guide member including a channel extending therethrough at an angle normal to a longitudinal axis of the arm portion when the guide member is connected to the arm portion;
    wherein the guide member is configured to be selectively moveable and lockable along a length of the arm portion
    wherein the arm portion includes indicia representing the relative height of the channel with respect to the bone tunnel when the elongated stem portion is inserted inside the bone tunnel;
    wherein the channel is configured to receive the trocar sleeve assembly comprising a trocar having a proximal end, a pointed distal end, an elongated body extending therebetween, and a sleeve disposed over the elongated body of the trocar, the channel further allowing moveable displacement of the trocar sleeve assembly through the guide member.

2. The assembly of claim 1, wherein the guide member includes two channels, and the assembly includes two trocar sleeve assemblies for placement of a trocar sleeve assembly in each channel, the aperture being sized to allow passage of two trocar sleeve assemblies theretlirough.

3. The assembly of claim 1, wherein the rod member is a cannulated rod.

4. The assembly of claim 1, wherein the trocar is removable from the sleeve.

5. The assembly of claim 1, wherein the guide member is configured to be slidably disposed along the length of the arm portion.

6. The assembly of claim 5, wherein the guide member further includes a locking mechanism for locking the guide member along the length of the arm portion.

7. The assembly of claim 6, wherein the locking mechanism comprises a set screw.

8. A method for fixing a tissue graft within a bone tunnel in a femoral bone, comprising the steps of:
    preparing a bone tunnel in the bone for insertion of a tissue graft;
    providing an adjustable drill guide assembly including a guide frame having an arm portion and a base portion that extends transversely to the arm portion, a rod member for connection to the base portion, the rod member extending transversely to the base portion and parallel to the arm portion when connected to the base portion, and further having an elongated stem portion having an enlarged head with an aperture therethrough for extending into the bone tunnel of the bone, and a guide member configured for connection to the arm portion, the guide member including a channel extending therethrough at an angle normal to a longitudinal axis of the arm portion when the guide member is connected to the arm portion, wherein the guide member is configured to be selectively moveable and lockable along a length of the arm portion;
    forming a bore transverse to the bone tunnel at a desired location near the entrance to the bone tunnel;
    placing the tissue graft inside the bone tunnel; and
    securing the tissue graft within the bone tunnel at the location of the bore.

9. The method of claim 8, wherein the step of forming a bore comprises the steps of placing the elongated stem portion into the bone tunnel, locking the guide member onto the arm portion, inserting a drill bit through the bore of the guide member, and drilling the hole so that the drill bit extends transversely through the bone tunnel.

10. The method of claim 9, further including the step of adjusting the guide member along the length of the arm portion, locking the guide member at another position on the arm portion, and drilling another bore transverse to the bone tunnel.

11. The method of claim 8, wherein the bore extends transversely through the bone tunnel at a distance between about 3 to 5 mm from the bone tunnel entrance.

12. The method of claim 8, wherein the bore extends transversely through the bone tunnel at a location near the bone tunnel exit.

13. The method of claim 8, wherein the step of securing the tissue graft comprises placing a cross pin through the bore to compress the tissue graft within the bone tunnel.

14. The method of claim 8, including the step of further securing the tissue graft to bone at a point near the bone tunnel exit.

15. The method of claim 14, wherein the tissue graft is further secured using a graft attachment device that is attached to the tissue graft.

16. The method of claim 15, wherein the graft attachment device anchors the tissue graft to a portion of the bone outside of the bone tunnel.

* * * * *